(12) United States Patent
Alizon et al.

(10) Patent No.: US 6,316,183 B1
(45) Date of Patent: *Nov. 13, 2001

(54) NUCLEIC ACID-BASED METHODS FOR THE DETECTION OF HUMAN IMMUNODEFICIENCY VIRUS TYPE 2 (HIV-2)

(76) Inventors: Marc Alizon, 71, rue du Cardinal Lemoine, 75005 Paris; Luc Montagnier, 21, rue de Malabry, Le Plessy Robinson; Denise Guetard, 4B rue Anselme Payen, 75015 Paris; Francoise Brun-Vezinet, 24 boulevard Saint-Germain, 75005 Paris, all of (FR); Francois Clavel, 12103 Portree Dr., Rockville, MD (US) 20852

( * ) Notice: Subject to any disclaimer, the term of this patent is extended or adjusted under 35 U.S.C. 154(b) by 0 days.

This patent is subject to a terminal disclaimer.

(21) Appl. No.: 08/467,161

(22) Filed: Jun. 6, 1995

Related U.S. Application Data (63) Continuation of application No. 08/132,919, filed on Oct. 7, 1993, now Pat. No. 5,545,726, which is a continuation of application No. 07/756,998, filed on Sep. 9, 1991, now Pat. No. 5,310,651, which is a continuation of application No. 07/602,383, filed on Oct. 24, 1990, now abandoned, which is a continuation of application No. 06/916,080, filed on Oct. 6, 1986, now abandoned, which is a continuation-in-part of application No. 06/835,228, filed on Mar. 3, 1986, now Pat. No. 4,839,288, which is a continuation of application No. 07/604,323, filed on Oct. 24, 1990, now abandoned, which is a continuation of application No. 06/933,184, filed on Nov. 21, 1986, now abandoned, which is a continuation-in-part of application No. 06/916,080, which is a continuation-in-part of application No. 06/835,228.

(30) Foreign Application Priority Data

| Jan. 22, 1986 | (FR) | 86 00911 |
| Jan. 22, 1986 | (FR) | 86 00910 |
| Feb. 6, 1986 | (FR) | 86 01635 |
| Feb. 13, 1986 | (FR) | 86 01985 |

(51) Int. Cl.$^7$ .............................. C12Q 1/68; C12Q 1/70
(52) U.S. Cl. ................ 435/5; 435/6; 536/23.72
(58) Field of Search .................. 435/5, 91.33, 91.51, 435/172.3, 6; 536/23.72, 24.1, 24.3

(56) References Cited

U.S. PATENT DOCUMENTS

| 5,310,651 | * | 5/1994 | Alizon et al. ........................... | 435/6 |
| 5,670,309 | | 9/1997 | Norrby et al. ........................... | 435/5 |

OTHER PUBLICATIONS

Kimmel, 1987, Meth. Enzymol. 152:393–396.*
Wahl et al., 1987, Meth. Enzymol. 152:399–407.*
Clavel et al. (1986, Nature 324:691–695.*

* cited by examiner

Primary Examiner—Laurie Scheiner
Assistant Examiner—Jeffrey S. Parkin (57) ABSTRACT

A method for diagnosing an HIV-2 (LAV-II) infection and a kit containing reagents for the same is disclosed. These reagents include cDNA probes which are capable of hybridizing to at least a portion of the genome of HIV-2. In one embodiment, the DNA probes are capable of hybridizing to the entire genome of HIV-2. These reagents also include polypeptides encoded by some of these DNA sequences.

6 Claims, 7 Drawing Sheets

```
                                      PvuI                 PstI
HIV.2  AGTAACTAACAGAA------ACAGCTGAGACTGC------AGGGACTTTCCAGAAGGGGCTG
       :::  :::::::  :::   :::::::::  :::     :::::::::::::::::: :
HIV.1  AGT-ACTTCAAGAACTGCTGACATC-GAGCTTGCTACAAGGGACTTTCCGCTGGGGACTT
                          9010           9020          9030     9040

HIV.2  TAACCAA-----------------GGGAGGGACATGGGAG------GAGCTGGTGGGGAACGCCTC
       :  :::   ::::::::::::::::::  :::::: :::            :::: ::::
HIV.1  T--CCAGGGAGGCGTGGCCTGGGCGGGACTGGGGAGTGGCGAGC------CCTC
       9050          9060           9070          9080    9090

HIV.2  ATATTCTCTGTATAAATATACCCGCTGCTTGCATTGTACTTCAGTCGCTCTGCGGAGAGG
       :  ::::::   :::    :::::::: :: :::: ::  :::::: :::: ::::
HIV.1  AGATG---CTGCATATAAAGCAGCTGCTTTTTGCC--TGTACTGG-GTCTCTCTGGTTAGAC-
       9100        9110              9120            9130 U3 R
                                                            R

HIV.2  CTGGCAGATTGAGCCCTGGGAGGTTCTCTCCAGCACTAGCAGGTAGAGCCTGGGTGTCCC
                ::::::   :::: ::::      :::  ::::::::::::::
HIV.1  ----CAGATTTGAGCCCTGGGAGC-TCTCTGGCTAACTAGGGAACCCAC-----------
           9150         9160          9170         9180      9190

HIV.2  TGCTAGACTCTCACCAGCACTTGGCCGGTGCTGGGCAGACGGCCCCACGCTTGCTTGCTT
                                                            :::::
HIV.1  -----------------------------------------------------TGCTT

HIV.2  AAAAACCTCCTT-----AATAAAGCT-GCC---AGTAGAAGCA
       :::          :::::::::::    :::   :::::::::
HIV.1  AAG------CCTCAATAAAGCTTGCCTTGAGTGCTTCAA◄
                         9210                9220        R|
                      Hind III
```

FIG. 5

NUCLEIC ACID-BASED METHODS FOR THE DETECTION OF HUMAN IMMUNODEFICIENCY VIRUS TYPE 2 (HIV-2)

This application is a continuation of application Ser. No. 08/132,919, filed Oct. 7, 1993, now U.S. Pat. No. 5,545,726, which is a continuation of application Ser. No. 07/756,998, filed Sept. 9, 1991, now U.S. Pat. No. 5,310,651, which is a continuation of application Ser. No. 07/602,383, filed Oct. 24, 1990, now abandoned, which is a continuation of application Ser. No. 06/916,080, filed Oct. 6, 1986, now abandoned, which is a continuation-in-part of application Ser. No. 06/835,228, filed Mar. 3, 1986, now U.S. Pat. No. 4,839,288; and a continuation of application Ser. No. 07/604,323, filed Oct. 24, 1990, now abandoned, which is a continuation of application Ser. No. 06/933,184, filed Nov. 21, 1986, now abandoned, which is a continuation-in-part of application Ser. No. 06/916,080, filed Oct. 6, 1986, now abandoned, which is a continuation-in-part of application Ser. No. 06/835,228, filed Mar. 3, 1986, now U.S. Pat. No. 4,839,288.

This application is a continuation of U.S. patent application Ser. No. 07/602,383 of Montagnier et al. for "Cloned DNA Sequences Related to the Genomic RNA of the Human Immunodeficiency Virus II (HIV-II), Polypeptides Encoded by these DNA Sequences and Use of these DNA Clones and Polypeptides in Diagnostic Kits," filed Oct. 24, 1990, which is a continuation of U.S. patent application Ser. No. 06/916, 080, filed Oct. 6, 1986, now abandoned, which is a continuation-in-part of U.S. patent application Ser. No. 06/835,228 of Montagnier et al. for "New Retrovirus Capable of Causing AIDS, Antigens Obtained from this Retrovirus and Corresponding Antibodies and their application for Diagnostic Purposes," filed Mar. 3, 1986, now U.S. Pat. No. 4,839,288. This application is also a continuation of U.S. patent application Ser. No. 07/604,323 of Alizon et al. for "Cloned DNA Sequences Related to the Entire Genomic RNA of Human Immunodeficiency Virus (HIV-II), Polypeptides Encoded by these DNA Sequences and Use of these DNA Clones and Polypeptides in Diagnostic Kits," filed Oct. 24, 1990, which is a continuation of U.S. patent application Ser. No. 06/933,184, filed Nov. 24, 1986, now abandoned, which is a continuation-in-part of U.S. patent application Ser. No. 06/916,080, filed Oct. 6, 1986, now abandoned, which is a continuation-in-part of U.S. patent application Ser. No. 06/835,228, filed Mar. 3, 1986, now U.S. Pat. No. 4,839,288. The contents of all applications and patents are incorporated herein by reference.

BACKGROUND OF THE INVENTION

The invention relates to cloned DNA sequences analogous to the genomic RNA of a virus known as Lymphadenopathy-Associated Virus II ("LAV-II"), a process for the preparation of these cloned DNA sequences, and their use as probes in diagnostic kits. In one embodiment, the invention relates to a cloned DNA sequence analogous to the entire genomic RNA of HIV-2 and its use as a probe. The invention also relates to polypeptides with amino acid sequences encoded by these cloned DNA sequences and the use of these polypeptides in diagnostic kits.

According to recently adopted nomenclature, as reported in Nature, May 1986, a substantially-identical group of retroviruses which has been identified as one causative agent of AIDS are now referred to as Human Immunodeficiency Viruses I (HIV-1). This previously-described group of retroviruses includes Lymphadenopathy-Associated Virus I (LAV-I), Human T-cell Lymphotropic Virus-III (HTLV-III), and AIDS-Related Virus (ARV).

Lymphadenopathy-Associated Virus II has been described in U.S. application Ser. No. 835,228, which was filed Mar. 3, 1986, and is specifically incorporated herein by reference. Because LAV-II is a second, distinct causative agent of AIDS, LAV-II properly is classifiable as a Human Immunodeficiency Virus II (HIV-2). Therefore, "LAV-II" as used hereinafter describes a particular genus of HIV-2 isolates.

While HIV-2 is related to HIV-1 by its morphology, its tropism and its in vitro cytopathic effect on CD4 (T4) positive cell lines and lymphocytes, HIV-2 differs from previously described human retroviruses known to be responsible for AIDS. Moreover, the proteins of HIV-1 and 2 have different sizes and their serological cross-reactivity is restricted mostly to the major core protein, as the envelope glycoproteins of HIV-2 are not immune precipitated by HIV-1-positive sera except in some cases where very faint cross-reactivity can be detected. Since a significant proportion of the HIV infected patients lack antibodies to the major core protein of their infecting virus, it is important to include antigens of both HIV-1 and HIV-2 in an effective serum test for the diagnosis of the infection by these viruses.

HIV-2 was first discovered in the course of serological research on patients native to Guinea-Bissau who exhibited clinical and immunological symptoms of AIDS and from whom sero-negative or weakly sero-positive reactions to tests using an HIV-1 lysate were obtained. Further clinical studies on these patients isolated viruses which were subsequently named "LAV-II."

One LAV-II isolate was deposited at the Collection Nationale des Cultures de Micro-Organismes (C.N.C.M.) at the Institut Pasteur, 28, Rue du Docteur Roux, in Paris, France on Dec. 19, 1985 under Accession No. I-502. A second LAV-II isolate was deposited at C.N.C.M. on Feb. 21, 1986 under Accession No. I-532. This second isolate has been subsequently referred to a LAV-II ROD. Several additional isolates have been obtained from West African patients, some of whom have AIDS, others with AIDS-related conditions and others with no AIDS symptoms. All of these viruses have been isolated on normal human lymphocyte cultures and some of them were thereafter propagated on lymphoid tumor cell lines such as CEM and MOLT.

Due to the sero-negative or weak sero-positive results obtained when using kits designed to identify HIV-1 infections in the diagnosis of these new patients with HIV-2 disease, it has been necessary to devise a new diagnostic kit capable of detecting HIV-2 infection, either by itself or in combination with an HIV-1 infection. The present inventors have, through the development of cloned DNA sequences analogous to at least a portion of the genomic RNA of LAV-II ROD viruses, created the materials necessary for the development of such kits.

SUMMARY OF THE INVENTION

As noted previously, the present invention relates to the cloned nucleotide sequences homologous or identical to at least a portion of the genomic RNA of HIV-2 viruses and to polypeptides encoded by the same. The present invention also relates to kits capable of diagnosing an HIV-2 infection.

Thus, a main object of the present invention is to provide a kit capable of diagnosing an infection caused by the HIV-2 virus.

This kit may operate by detecting at least a portion of the RNA genome of the HIV-2 virus or the provirus present in the infected cells through hybridization with a DNA probe or it may operate through the immunodiagnostic detection of polypeptides unique to the HIV-2 virus.

Additional objects and advantages of the present invention will be set forth in part in the description which follows, or may be learned from practice of the invention. The objects and advantages may be realized and attained by means of the instrumentalities and combinations particularly pointed out in the appended claims.

To achieve these objects and in accordance with the purposes of the present invention, cloned DNA sequences related to the entire genomic RNA of the LAV-II virus are set forth. These sequences are analogous specifically to the entire genome of the LAV-II ROD strain.

To further achieve the objects and in accordance with the purposes of the present invention, a kit capable of diagnosing an HIV-2 infection is described. This kit, in one embodiment, contains the cloned DNA sequences of this invention which are capable of hybridizing to viral RNA or analogous DNA sequences to indicate the presence of an HIV-2 infection. Different diagnostic techniques can be used which include, but are not limited to: (1) Southern blot procedures to identify cellular DNA which may or may not be digested with restriction enzymes; (2) Northern blot techniques to identify RNA extracted from cells, body fluids or culture supernatants; and (3) dot blot techniques, i.e., direct filtration of the sample through an ad hoc membrane such as nitrocellulose or nylon without previous separation on agarose gel. Suitable material for dot blot technique could be obtained from body fluids including, but not limited to, serum and plasma, supernatants from culture cells, or cytoplasmic extracts obtained after cell lysis and removal of membranes and nuclei of the cells by centrifugation as accomplished in the "CYTODOT" procedure as described in a booklet published by Schleicher and Schull.

In an alternate embodiment, the kit contains the polypeptides created using these cloned DNA sequences. These polypeptides are capable of reacting with antibodies to the HIV-2 virus present in sera of infected individuals, thus yielding an immunodiagnostic complex.

It is understood that both the foregoing general description and the following detailed description are exemplary and explanatory only and are not restrictive of the invention as claimed. The accompanying drawings, which are incorporated in and constitute a part of the specification, illustrate one embodiment of the invention and, together with the description, serve to explain the principles of the invention.

BRIEF DESCRIPTION OF THE DRAWINGS

FIGS. 1A and 1B generally depict the nucleotide sequence of a cloned complementary DNA (cDNA) to the genomic RNA of HIV-2. FIG. 1B depicts the nucleotide sequence of the 3' end of the 3' LTR of HIV-2. The corresponding region of the HIV-1 LTR was aligned using the Wilburg and Lipman algorithm (window: 10; K-tuple: 7; gap penalty: 3 as described by U. Gublu and B. J. Hoffman in Gene 25: 263–269 (1983), specifically incorporated herein by reference). The U3-R junction in HIV-1 is indicated and the poly A addition signal and potential TATA promoter regions are boxed. In FIG. 1A, the symbols B, H, Ps and Pv refer to the restriction sites BamHI, HindIII, PstI and PvuII, respectively.

FIGS. 2A, 2B, 2C, and 2D generally depicts the HIV-2 specificity of the E2 clone. FIGS. 2A and 2C depict hybridization with the HIV-2 cDNA (E2) and FIGS. 2B and 2D depict hybridization to an HIV-1 probe consisting of a 9.2 Kb SacI insert from HIV-$1_{BRU}$.

FIGS. 3A and 3B generally depict a restriction map of the HIV-$2_{ROD}$ genome and its homology to HIV-1. In FIG. 3A, the open boxes represent viral sequences, the LTR are filled, and the dotted boxes represent cellular flanking sequences (not mapped). Only some characteristic restriction enzyme sites are indicated. ROD 27 and 35 are derived from integrated proviruses while ROD 4 is derived from a circular viral DNA. The portion of the lambda clones that hybridizes to the cDNA E2 is indicated below the maps. A restriction map of the $\lambda$ROD isolate was reconstructed from these three lambda clones. In this map, the restriction sites are identified as follows: B: BamHI; E: EcoRI; H: HindIII; K: KpnI; Ps: PstI; Pv: PvuII; S: SacI; X: XbaI. R and L are the right and left BamHI arms of the lambda L47.1 vector.

FIG. 3B specifically depicts dots 1–11 which correspond to the single-stranded DNA form of M13 subclones from the HIV-$1_{BRU}$ cloned genome. Their size and position on the HIV-1 genome, determined by sequencing is shown below the figure. Dot 12 is a control containing lambda phage DNA. The dot-blot was hybridized in low stringency conditions as described in Example 3 with the complete lambda ROD 4 clone as a probe, and successively washed in 2×SSC, 0.1% SDS at 25° C. (Tm −42° C.), 1×SSC, 0.1% SDS at 60° C. (Tm −20° C.), and 0.1×SSC, 0.1% SDS at 60° C. (Tm −3° C.) and exposed overnight. A duplicate dot blot was hybridized and washed in stringent conditions (as described in Example 4) with the labelled lambda J19 clone carrying the complete HIV-$1_{BRU}$ genome. HIV-1 and HIV-2 probes were labelled the same specific activity ($10^8$ cpm/$\mu$g.).

FIGS. 4A and 4B generally depict the restriction map polymorphism in different HIV-2 isolates and shows comparison of HIV-2 to SIV.

FIG. 4B specifically depicts DNA from HUT 78 (a human T lymphoid cell line) cells infected with SIV Mm 142–83. The same amounts of DNA and enzymes were used as used in panel A. Hybridization was performed with the same probe as in A, but in non-stringent conditions. As described in Example 3 washing was for one hour in 2×SSC, 0.1% SDS at 40° C. (panel 1) and after exposure, the same filter was re-washed in 0.1×SSC, 0.1% SDS at 60° C. (panel 2). The autoradiographs were obtained after overnight exposure with intensifying screens.

DETAILED DESCRIPTION OF THE PREFERRED EMBODIMENTS

Reference will now be made in detail to the presently preferred embodiments of the invention, which, together with the following examples, serve to explain the principles of the invention.

Figure 5:
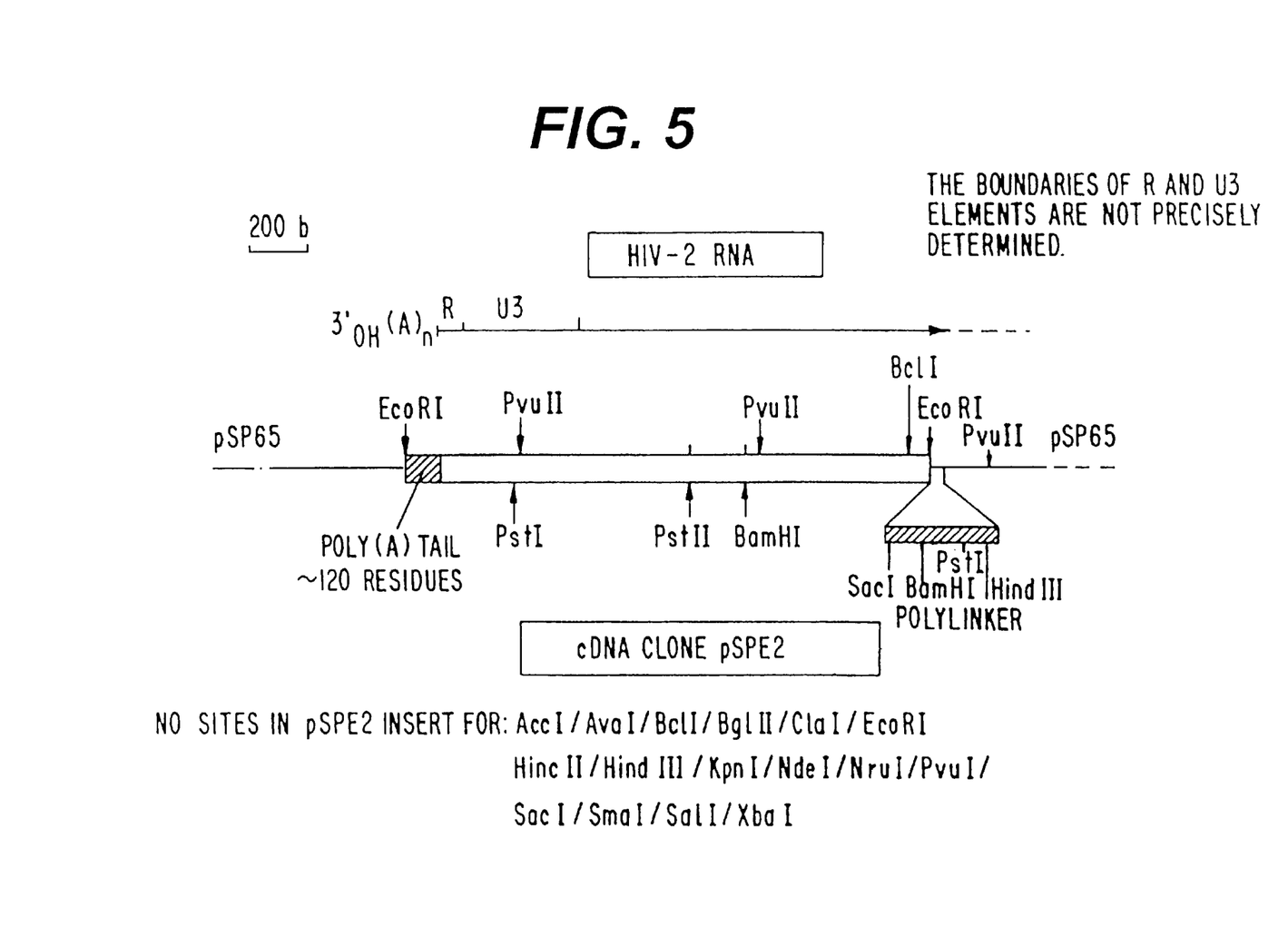
FIG. 5 is a restriction map of the LAV-II ROD genome.

The genetic sequence of a portion of the HIV-2 virus has been determined according to the method set forth in the examples. A restriction map of the genome of this virus is set forth in FIG. 5. In addition, a portion of this sequence, in particular the poly A tail, the end of the U3 region and the total R region have been sequenced. This sequence information is included in Example 2, infra.

From this sequence data, certain regions have been identified which are capable of being used as probes in diagnostic methods to obtain the immunological reagents necessary to diagnose an HIV-2 infection. In particular, these probes may be used in hybridization reactions with the genetic material of infected patients to indicate whether the RNA of the HIV-2 virus is present in these patients' lymphocytes. In this embodiment, the test methods which may be utilized include Northern blots, Southern blots and dot blots.

In addition, the genetic sequences of the HIV-2 virus may be used to create the polypeptides encoded by these sequences. Specifically, these polypeptides may be created by expression of the cDNA obtained in the following Examples in hosts such as bacteria, yeast or animal cells. These polypeptides may be used in diagnostic tests such as immunofluorescense assays (IFA), radioimmunoassays (RIA) and Western blot tests. One particular polypeptide which is useful in these diagnostic procedures is the expression product of the cDNA clone analogous to the total R region of the HIV-2 genome.

In addition to the cDNA sequences described in the following examples, other DNA and/or RNA sequences can be isolated which will be identical or homologous to the genome of various HIV-2 isolates. These new sequences also may serve as the basis for additional immunodiagnostic and probe tests of the type described above. These other DNA and/or RNA sequences may be isolated according to methods routinely known to those of ordinary skill in the art once they have been apprised of the teachings contained herein.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

The genetic structure of the HIV-2 virus has been analyzed by molecular cloning according to the method set forth herein and in the Examples. A restriction map of the genome of this virus is included in FIG. 4. In addition, the partial sequence of a cDNA complementary to the genomic RNA of the virus has been determined. This cDNA sequence information is included in FIG. 1.

Also contained herein is data describing the molecular cloning of the complete 9.5 kb. genome of HIV-2, data describing the observation of restriction map polymorphism between different isolates, and an analysis of the relationship between HIV-2 and other human and simian retroviruses. From the totality of these data, diagnostic probes can be discerned and prepared.

Generally, to practice one embodiment of the present invention, a series of filter hybridizations of the HIV-2 RNA genome with probes derived from the complete cloned HIV-1 genome and from the gag and pol genes were conducted. These hybridizations yielded only extremely weak signals even in conditions of very low stringency of hybridization and washing. Thus, it was found to be difficult to assess the amount of HIV-2 viral and proviral DNA in infected cells by Southern blot techniques.

Therefore, a complementary DNA (cDNA) to the HIV-2 genomic RNA initially was cloned in order to provide a specific hybridization probe. To construct this cDNA, an oligo (dT) primed cDNA first-strand was made in a detergent-activated endogenous reaction using HIV-2 reverse transcriptase with virions purified from supernatants of infected CEM cells. The CEM cell line is a lymphoblastoid CD4+ cell line described by G. E. Foley et al. in *Cancer* 18: 522–529 (1965), specifically incorporated herein by reference. The CEM cells used were infected with the isolate ROD and were continuously producing high amounts of HIV-2.

After second-strand synthesis, the cDNAs were inserted into the TG130 ml3 bacteria phage vector. A collection of $10^4$ M13 recombinant phages was obtained and screened in situ with an HIV-1 probe spanning 1.5 kb of the 3' end of the $LAV_{BRU}$ isolate (depicted in FIG. 1A). Some 50 positive plaques were detected, purified, and characterized by end sequencing and crosshybridizing the inserts. This procedure is described in more detail in Example 3 and in FIG. 1.

The different clones were found to be complementary to the 3' end of a polyadenylated RNA having the AATAAA signal about 20 nucleotides upstream of the poly A tail, as found in the long terminal repeat (LTR) of HIV-1. The LTR region of HIV-1 has been described by S. Wain Hobson et al. in *Cell* 40: 9–17 (1985), specifically incorporated herein by reference. The portion of the HIV-2 LTR that was sequenced was related only distantly to the homologous domain in HIV-1 as demonstrated in FIG. 1B. Indeed, only about 50% of the nucleotides could be aligned and about a hundred insertions/deletions need to be introduced. In comparison, the homology of the corresponding domains in HIV-1 isolates from USA and Africa is greater than 95% and no insertions or deletions are seen.

The largest insert of this group of M13 clones was a 2 kb clone designated E2. Clone E2 was used as a probe to demonstrate its HIV-2 specificity in a series of filter hybridization experiments. Firstly, this probe could detect the genomic RNA of HIV-2 but not HIV-1 in stringent conditions as shown in FIG. 2, C and D. Secondly, positive signals were detected in Southern blots of DNA from cells infected with the ROD isolate as well as other isolates of HIV-2 as shown in FIG. 2, A and FIG. 4, A. No signal was detected with DNA from uninfected cells or HIV-1 infected cells, confirming the exogenous nature of HIV-2. In undigested DNA from HIV-2 infected cells, an approximately 10 kb species, probably corresponding to linear unintegrated viral DNA, was principally detected along with a species with an apparent size of 6 kb, likely to be the circular form of the viral DNA. Conversely, rehybridization of the same filter with an HIV-1 probe under stringent conditions showed hybridization to HIV-1 infected cells only as depicted in FIG. 2, B.

To isolate the remainder of the genome of HIV-2, a genomic library in lambda phage L47.1 was constructed. Lambda phage L47.1 has been described by W. A. M. Loenen et al. in *Gene* 10: 249–259 (1980), specifically incorporated herein by reference. The genomic library was constructed with a partial Sau3AI restriction digest of the DNA from the CEM cell line infected with HIV-$2_{ROD}$.

About 2×10⁶ recombinant plaques were screened in situ with labelled insert from the E2 cDNA clone. Ten recombinant phages were detected and plaque purified. Of these phages, three were characterized by restriction mapping and Southern blot hybridization with the E2 insert and probes from its 3' end (LTR) or 5' end (envelope), as well as with HIV-1 subgenomic probes. In this instance, HIV-1 probes were used under non-stringent conditions.

Figure 3A:
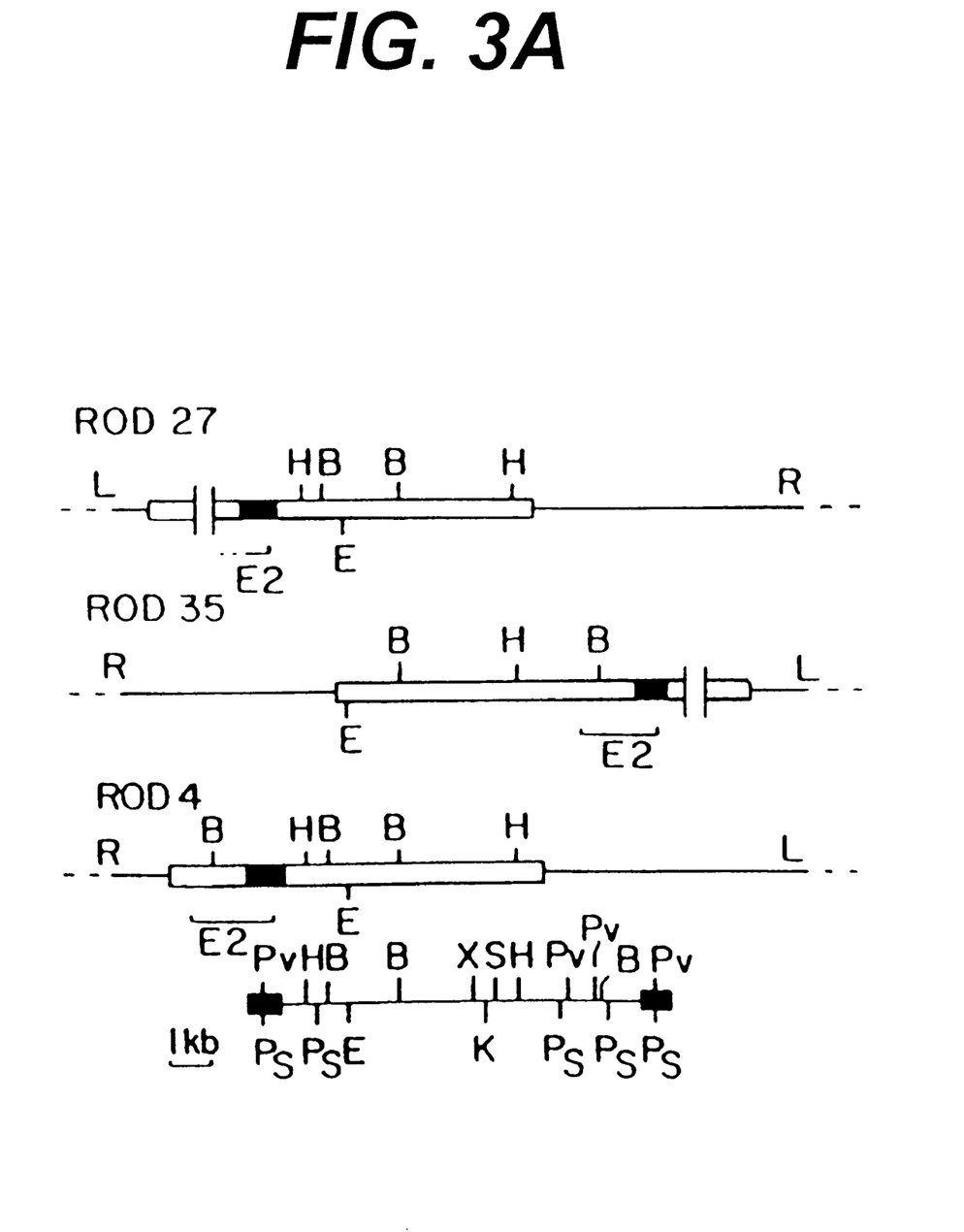
FIG. 3A specifically depicts the organization of three recombinant phage lambda clones, ROD 4, ROD 27, and ROD 35.

A clone carrying a 9.5 kb. insert and derived from a circular viral DNA was identified as containing the complete genome and designated λROD 4. Two other clones, λROD 27 and λROD 35 were derived from integrated proviruses and found to carry an LTR and cellular flanking sequences and a portion of the viral coding sequences as shown in FIG. 3, A. The λROD 4 fragment containing the genome of HIV-2 may be found in the genome of the plasmid pROD 4.7 in $E.$ $coli$ $TG_1$ stored under C.N.C.M. I-627; the λROD 27 fragment may be found in the genome of the plasmid pROD 27.5 in $E.$ $coli$ HB101 stored under C.N.C.M. I-626; and another ROD fragment containing the genome of HIV-2 may be found on plasmid pROD 4.8 in $E.$ $coli$ $TG_1$ stored under C.N.C.M I628 (all deposits made Nov. 21. 1986).

Figure 1A:
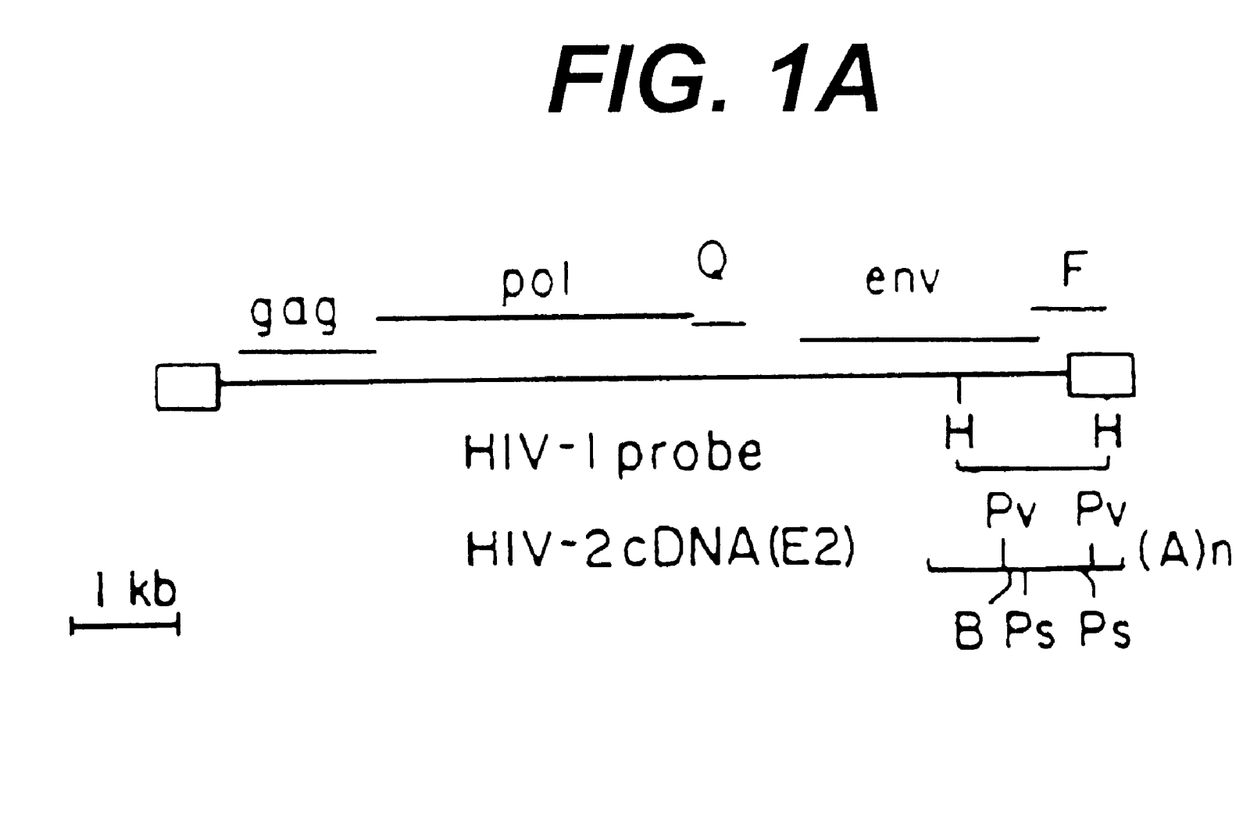
FIG. 1A depicts the genetic organization of HIV-1, position of the HIV-1 HindIII fragment used as a probe to screen the CDNA library, and restriction map of the HIV-2 cDNA clone, E2.
Figure 1B:
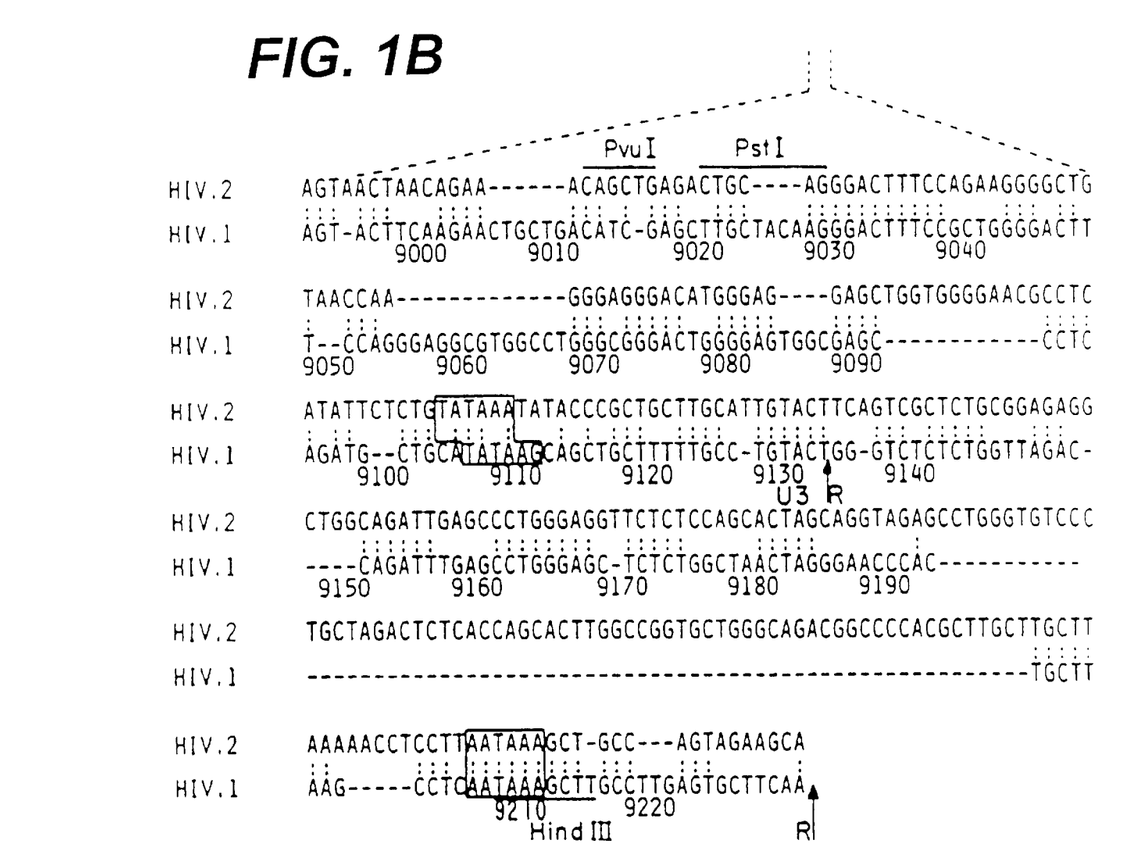
Figure 3B:
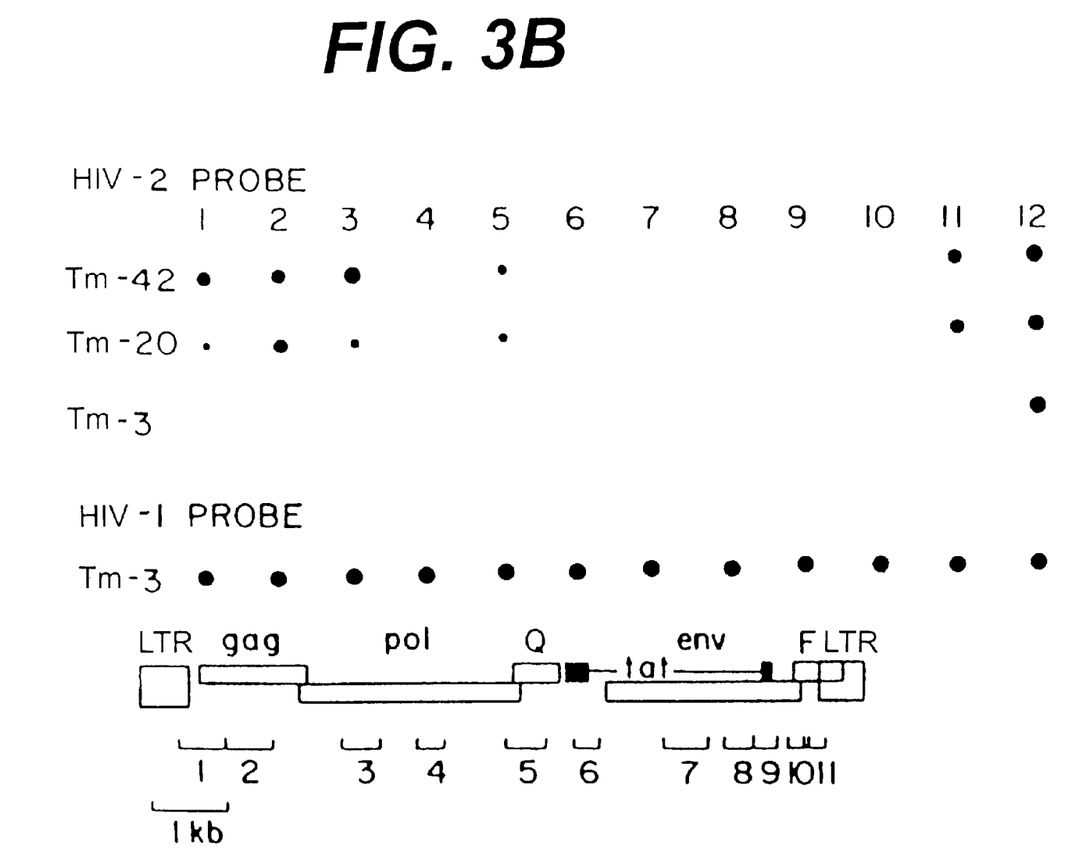

The relationship of HIV-2 to other human and simian retro-viruses was surmised from hybridization experiments. The relative homology of the different regions of the HIV-1 and 2 genomes was determined by hybridization of fragments of the cloned HIV-1 genome with the labelled λROD 4 expected to contain the complete HIV-2 genome (FIG. 3, B). Even in very low stringency conditions (Tm −42° C.), the hybridization of HIV-1 and 2 was restricted to a fraction of their genomes, principally the gag gene (dots 1 and 2), the reverse transcriptase domain in pol (dot 3), the end of pol and the Q (or sor) genes (dot 5) and the F gene (or 3' orf) and 3' LTR (dot 11). The HIV-1 fragment used to detect the HIV-2 cDNA clones contained the dot 11 subclone, which hybridized well to HIV-2 under non-stringent conditions. Only the signal from dot 5 persisted after stringent washing. The envelope gene, the region of the tat gene and a part of pol thus seemed very divergent. These data, along with the LTR sequence obtained (FIG. 1, B), indicated that HIV-2 is not an envelope variant of HIV-1 as described by M. Alizon et al. in Cell 46: 63–74 (1986).

It was observed that HIV-2 is related more closely to the Simian Immunodeficiency Virus (SIV) than it is to HIV-1. This correlation has been described by F. Clavel et al. in C.R. Acad. Sci. (Paris) 302: 485–488 (1986) and F. Clavel et al. in Science 233: 343–346 (1986), both of which are specifically incorporated herein by reference. Simian Immunodeficiency Virus (also designated Simian T-cell Lymphotropic virus Type 3, STLV-3) is a retrovirus first isolated from captive macaques with an AIDS-like disease in the USA. This simian virus has been described by M. D. Daniel et al. in Science 228: 1201–1204 (1985), specifically incorporated herein by reference.

All the SIV proteins, including the envelope, are immune precipitated by sera from HIV-2 infected patients, whereas the serological cross-reactivity of HIV-1 to 2 is restricted to the core proteins. However SIV and HIV-2 can be distinguished by slight differences in the apparent molecular weight of their proteins.

Figure 2A:
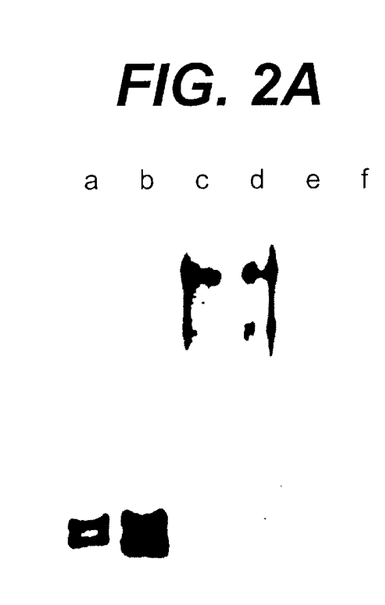
FIGS. 2A and 2B specifically depict a Southern blot of DNA extracted from CEM cells infected with the following isolates: $\lambda$HIV-$2_{ROD}$ (a,c), HIV-$2_{DUL}$ (b,d), and HIV-$1_{BRU}$ e, f. Blots a, b, f are PstI digested. Blots c, d, e are undigested.
Figure 2B:
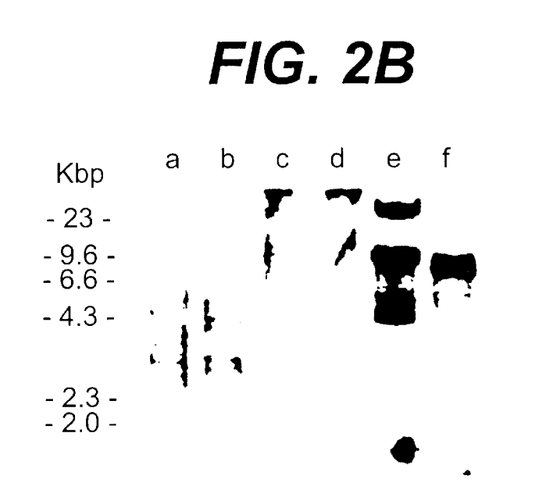
Figure 2C:
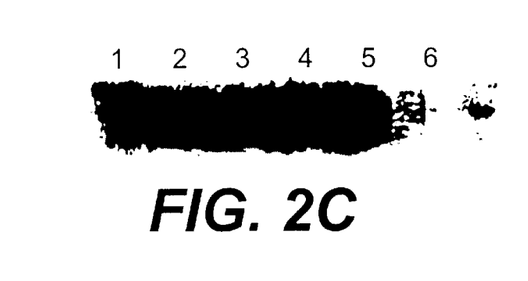
FIGS. 2C and 2D specifically depict dot blot hybridization of pelleted virions from CEM cells infected by the HIV-$1_{BRU}$(1), SIV isolate Mm 142–83 (3), HIV-$2_{DUL}$ (4), $\lambda$HIV-$2_{ROD}$ (5), and HIV-$1_{ELI}$ (6). Dot 2 is a pellet from an equivalent volume of supernatant from uninfected CEM. Thus.
Figure 2D:
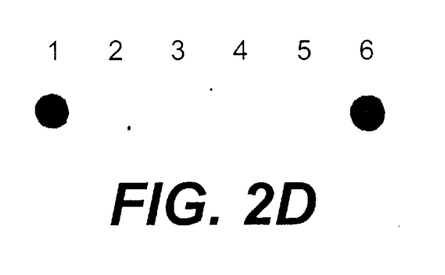

In terms of nucleotide sequence, it also appears that HIV-2 is closely related to SIV. The genomic RNA of SIV can be detected in stringent conditions as shown in FIG. 2, C by HIV-2 probes corresponding to the LTR and 3' end of the genome (E2) or to the gag or pol genes. Under the same conditions, HIV-1 derived probes do not detect the SIV genome as shown in FIG. 2, D.

In Southern blots of DNA from SIV-infected cells, a restriction pattern clearly different from HIV-$2_{ROD}$ and other isolates is seen. All the bands persist after a stringent washing, even though the signal is considerably weakened, indicating a sequence homology throughout the genomes of HIV-2 and SIV. It has recently been shown that baboons and macaques could be infected experimentally by HIV-2, thereby providing an interesting animal model for the study of the HIV infection and its preventive therapy. Indeed, attempts to infect non-human primates with HIV-1 have been successful only in chimpanzees, which are not a convenient model.

Figure 4A:
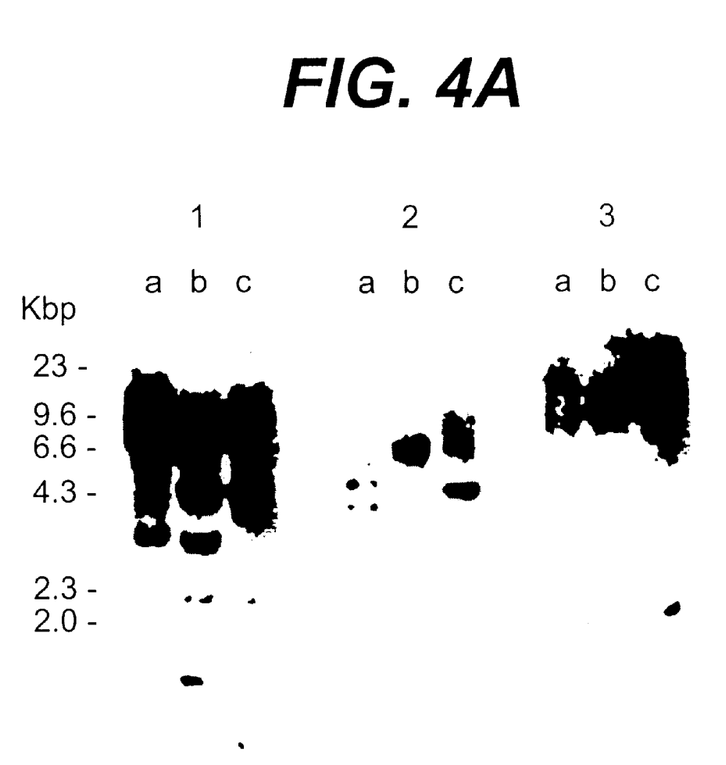
FIG. 4A specifically depicts DNA (20 $\mu$g per lane) from CEM cells infected by the isolate HIV-$2_{DUL}$ (panel 1) or peripheral blood lymphocytes (PBL) infected by the isolates HIV-$2_{GOM}$ (panel 2) and HIV-$2_{MIR}$ (panel 3) digested with: EcoRI (a), PstI (b), and HindIII (c). Much less viral DNA was obtained with HIV-2 isolates propogated on PBL. Hybridization and washing were in stringent conditions, as described in Example 4, with $10^6$ cpm/ml of each of the E2 insert (cDNA) and the 5 kb. HindIII fragment of $\lambda$ROD 4, labelled to $10^9$ cpm/$\mu$g.

From an initial survey of the restriction maps for certain of the HIV-2 isolates obtained according to the methods described herein, it is already apparent that HIV-2, like HIV-1, undergoes restriction site polymorphism. FIG. 4A depicts examples of such differences for three isolates, all different one from another and from the cloned HIV-$2_{ROD}$. It is very likely that these differences at the nucleotide level are accompanied by variations in the amino acid sequence of the viral proteins, as evidenced in the case of HIV-1 and described by M. Alizon et al. in Cell 46: 63–74 (1986), specifically incorporated herein by reference.

Further, the characterization of HIV-2 will also delineate the domain of the envelope glycoprotein that is responsible for the binding of the surface of the target cells and the subsequent internalization of the virus. This interaction was shown to be mediated by the CD4 molecule itself in the case of HIV-1 and similar studies tend to indicate that HIV-2 uses the same receptor. Thus, although there is wide divergence between the env genes of HIV-1 and 2, small homologous domains of the envelopes of the two HIV could represent a candidate receptor binding site. This site could constitute a target for use to raise a protective immune response against this group of retroviruses.

Figure 4B:
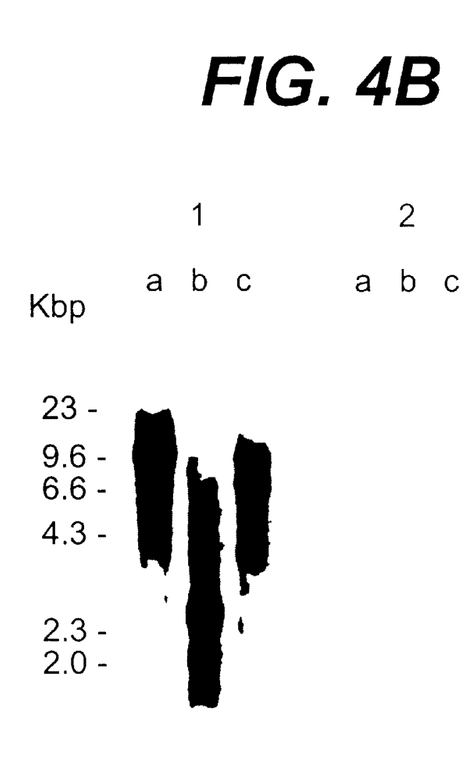

From the data discussed herein, certain nucleotide sequences have been identified which are capable of being used as probes in diagnostic methods to obtain the immunological reagents necessary to diagnose an HIV-2 infection. In particular, these sequences may be used as probes in hybridization reactions with the genetic material of infected patients to indicate whether the RNA of the HIV-2 virus is present in these patient's lymphocytes or whether an analogous DNA is present. In this embodiment, the test methods which may be utilized include Northern blots, Southern blots and dot blots. One particular nucleotide sequence which may be useful as a probe is the combination of the 5 kb. HindIII fragment of λROD 4 and the E2 cDNA used in FIG. 4.

In addition, the genetic sequences of the HIV-2 virus may be used to create the polypeptides encoded by these sequences. Specifically, these polypeptides may be created by expression of the cDNA obtained according to the teachings herein in hosts such as bacteria, yeast or animal cells. These polypeptides may be used in diagnostic tests such as immunofluorescence assays (IFA), radioimmunoassays (RIA) and Western blot tests.

Moreover, it is also contemplated that additional diagnostic tests, including additional immunodiagnostic tests, may be developed in which the DNA probes or the polypeptides of this invention may serve as one of the diagnostic reagents. The invention described herein includes these additional test methods.

Thus, it is to be understood that application of the teachings of the present invention to a specific problem or environment will be within the capabilities of one having ordinary skill in the art in light of the teachings contained herein. Examples of the products of the present invention and representative processes for their isolation and manufacture appear above and in the following examples.

EXAMPLES

Example 1

To prepare DNA probes for use in HIV-2 diagnostic kits, a cDNA complementary to genomic RNA obtained from purified virions was prepared by the following method.

Supernatant from a 48 hour culture of CEM cells infected with the HIV-2 isolate LAV-II ROD was ultracentrifuged. The virion-containing pellet was then banded on a sucrose gradient and repelleted using substantially the same method as disclosed in U.S. patent application Ser. No. 835,228, supra.

The purified HIV-2 preparation was used for the synthesis of CDNA through an endogenous, detergent-activated reaction. Briefly, the virion preparation was added to a reaction mixture containing 50 µM Tris-HCl, 5 mM $MgCl_2$, 10 mM DTT, 0.025% Triton, and 50 µM each of the 4 deoxynucleoside triphosphates and oligo (dT) primer. The reaction was carried out for 90 minutes at 37° C.

After phenol extraction of the proteins present in this first reaction mixture, the second strand of the cDNA was synthesized in the presence of RNAse H, E. coli DNA polymerase I, and four deoxynucleotides for 1 hour at 15° C. and 1 hour at 22° C. Blunt ends were created on this double-stranded cDNA by the action of T4 DNA polymerase. All reagents for this procedure were purchased from Amersham (Amersham cDNA kit) and used as recommended by the supplier.

After (1) ligation of EcoRI linkers (obtained from Pharmacia) to these blunt ends with T4 DNA ligase (obtained from Biolabs), (2) digestion of the linkers by the restriction endonuclease EcoRI, and (3) elimination of linker fragments by gel filtration on Ultrogel AcA 34 column (LKB-IBF), the cDNA was inserted into a EcoRI-cut Tg130 M13 vector (obtained from Amersham). A cDNA library was obtained after transformation of E. coli TG1 strain. Approximately 104 recombinant M13 plaques were obtained.

To screen this cDNA library to detect the presence of HIV-2 cDNA-containing recombinant M13 clones, the plaque hybridization technique was used. Briefly, the DNA from M13 plaques was transferred to nitrocellulose filters, and was hybridized to a subgenomic HIV-1 probe derived from clone LAV lambda J19. This probe was comprised of the DNA located between two HindIII restriction sites within the env open reading frame and the R segment of the 3' LTR. This probe contains the 3' end of the env gene, the whole F gene, the U3 segment and part of the R segment of the LTR, and is approximately 1500 bp long.

The probe was obtained by labelling the 1.5 kb HindIII insert with 32P dCTP and dTTP (3000 Ci×10−3 mole) using random primer and Klenow DNA polymerase 1 in a 4 hour incubation at 15° C. (using a kit obtained from Amersham). The hybridization was carried out overnight in low stringency conditions in a hybridization mixture containing 5×SSC, 5×Denhart solution, 25% formamide, 100 µg/ml denatured salmon sperm DNA, and the labelled probe (2×107 cpm at specificity 109 cpm/µg) at 37° C. The filters were washed out in three successive wash procedures as set forth below. Each wash was followed by autoradiography of the filters.

Wash #1: 5×SSC, 0.1% SDS, at 25° C. for 4×15 minutes.
Wash #2: 2×SSC, 0.1% SDS, at 42° C. for 2×30 minutes.
Wash #3: 0.1×SSC, 0.1% SDS, at 65° C. for 2×30 minutes.

Several positive clones were detected after wash #1, which were still detected after wash #2. However, all signals disappeared after wash #3. This indicated that the positive clones were related only distantly to the genome of HIV-1. These positive clones were picked up, replated, and rehybridized with the same probe in the same stringency conditions as wash #1. The majority of them were found still to be positive.

The clones were also screened with a total human DNA probe, in medium stringency conditions using the following procedure: hybridization in 5×SSC, 5×Denhart, and 40% formamide followed by washing in 1×SSC, 0.1% SDS, at 50° C. None of the previously positive clones could be detected and therefore did not correspond to repetitive DNA species or cDNA to ribosomal RNA.

The positive recombinant M13 clones were grown in liquid medium and characterized in different ways:

(1) Size of their insert: M13 single-stranded template DNA was obtained from each individual clone, and second strand synthesis was conducted with the 17-mer M13 sequence primer and Klenow enzyme. The inserts were excised by EcoRI (Boehringer) and analyzed by electrophoresis on agarose gel. Most inserts were between 600 and 200 bp, except the insert of clone E2.1, which is approximately 2 Kbp long.

(2) Nucleotide sequence analysis: Several clones have been partially sequenced, using the dideoxy method of Sanger et al. as reported in *Proc. Natl. Acad. Sci.* 74:5463–7 (1977), specifically incorporated herein by reference. Different independent clones exhibit a similar nucleotide sequence except for the presence of poly-A chains of different length at their 3' end. This demonstrates that these are cDNA clones from the same RNA template. The detailed sequence analysis of these cDNA clones, which should correspond to the 3' end of the HIV-2 genome, has shown only a limited homology to HIV-1.

(3) Hybridization with HIV-2 genomic RNA and DNA (a) Obtaining HIV-2 genomic RNA: The infected supernatant was pelleted (50,000 rotations, 30 minutes). The pellet was resuspended in 10 mM Tris pH 7.5, 1 mM EDTA, 0.1% SDS. One of the insert clones F1.1 was labelled, and used as a probe for hybridization with genomic RNA from different viral isolates according to the dot-blot technique. The dot-blot technique consists of the following steps: (i) Spotting the sample (HIV-2 lysate) on a nitrocellulose membrane previously soaked in 20×SS (3M NaCl, 0.3M sodium citrate) and air dried, (ii) baking the membrane for 2 hours at 80° C., and (iii) hybridization. This hybridization was conducted under high stringency conditions (5×SSC, 5×Denhart, 50% formamide at 42° C.), followed by washing in 0.1×SSC, 0.1% SDS at 65° C. Under these conditions, the probe hybridized strongly to spots from two independent isolates of HIV-2, including LAV-II ROD, from which the cloned cDNA was derived. A faint hybridization signal was detected with the spot from STLV-IIImac (Simian T-Lymphotropic Virus (also known as "SIV") Type III, macaque), and no hybridization was detectable with two isolates of HIV-1.

Southern blot experiments using E2.1 insert (2 Kb) as a $^{32}$p labelled probe did not show detection of hybridization with DNA from uninfected cells but detected band in HIV-2 detached cells in high stringency conditions. HIV-2 shows a polymorphism on the same level of the restriction map as HIV-1. With complete cellular DNA from infected cells, two kinds of signals were detected by Southern blot: (1) in the DNA fraction MW approximately 20 kb and over which is the virus integrated form, and (2) in the fraction of low MW

Example 2

The cDNA obtained from Example 1 was determined to have the following nucleotide sequence:

```
           10        20        30        40        50        60        70        80        90       100
GTGGAAGGCGAGACTGAAAGCAAGAGGAATACCATTTAGTTAAAGGACAGGAACAGCTATACTTGGTCAGGGCAGGAAGTAACTAACAGAAACAGCTGAG

MNLI                               ALUI                 MAEIII     PVUII
                                                                                    ALUI
                                                                                      DDEI 110       120       130       140       150       160       170       180       190       200
ACTGCAGGGACTTTCCAGAAGGGGCTGTAACCAAGGGAGGGACATGGGAGGAGCTGGTGGGGAACGCCTCATATTCTCTGTATAATATACCCGCTGCTTG

PSTI                  MAEIII   MNLI NLAIII ALUI            MNLI                         BBVI
                           STYI             MNLI                                           FNU4HI
                                                                                           TTH111III 210       220       230       240       250       260       270       280       290       300
CATTGTACTTCAGTCGCTCTGCGGAGAGGCTGGCAGATTGAGCCCTGGAGGATCTCTCCAGCACTAGACGGATGAGCCTGGGTGCCCTGCTAGACTCTCA

RSAI               MNLI          BANII   MNLI         MAEI       APYI BSP1286 MAEI    HPHI
                                         BSP1286  XHOII                   BSTNI        HINFI
                                          APYI    DPNI                    ECORII
                                         BSTNI    MBOI                    SCRFI
                                         ECORII   NDEII                    BANI
                                         SCRFI    SAUIIIA 310       320       330       340       350       360       370       380
CCAGCACTTGGCCGGTGCTGGCAGACGGCCCCACGCTTGCCTGCTTAAAAACCTTCCTTAATAAAGCTGCAGTAGAAGCA

HAEIII        HAEIII                                ALUI
             HAPII         SAU96A                                BBVI
             HPAII                                               FNU4HI
             MSPI
```

(9,10 kb) which is virus non-integrated in the genome. This pattern is highly characteristic of a retrovirus. Some experiments performed with STLV-III (SIV-3) infected cells showed that the simian retrovirus is distantly related to HIV-2 (the signal was only detected in low stringency conditions). These experiments demonstrate that the probe is specific for HIV-2.

(4) Subcloning of HIV-2 cDNA into a bacterial plasmid vector: one particular positive M13, E21, was selected, and subcloned into a plasmid vector. This clone has been referred to as pSPE2 and was deposited at the C.N.C.M. in Paris, France, under Accession No. I-595 on Sept. 5, 1986. The DNA of phage M13 (TG 130) recombinant E-2 was purified as a single-stranded DNA of the clone containing 2 kb to the 3' prime portion of the genome of HIV-2 (LAV-II ROD isolate) already inserted in the phage M-13 (TG130) (obtained from Amersham). This DNA was transferred to the plasmid pSP65, as described by Melton, D. A. in 357 *Nucleic Acid Res.* 12:035–7056 (1984). Using this technique, the DNA from the M13 recombinant phage was purified and labeled M-13-ROD-E2. In vitro, a second strand was constructed, using 17 mer sequence primer (Amersham), the four nucleotides ACTG, and the DNA polymerase I (Klenow). The EcoRI insert was excised by EcoRI digestion and purified on agarose gel and ligated to pSP65. The pSP65 vector previously was digested with EcoRI. This ligation mixture was used to transform into *E. coli* DH1 strain, and recombinants were selected for their ability to demonstrate resistance to ampicillin. The identified recombinants were cultured in a LB (Luria medium) containing 50 µg/ml ampicillin and the recombinant plasmids were purified and controlled the presence of the correct insert.

Example 3

Cloning of a cDNA Complementary to Genomic RNA From HIV-2 Virions

HIV-2 virions were purified from 5 liters of supernatant from a culture of the CEM cell line infected with the ROD isolate and a cDNA first strand using oligo (dT) primer was synthesized in detergent activated endogenous reaction on pelleted virus, as described by M. Alizon et al. in *Nature*, 312: 757–760 (1984), specifically incorporated herein by reference. RNA-cDNA hybrids were purified by phenol-chloroform extraction and ethanol precipitation. The second-strand cDNA was created by the DNA polymerase I/RNAase H method of Sanger et al. described in *Proc. Nat'l. Acad. Sci. USA*, 74: 5463–5467 (1977), specifically incorporated herein by reference. The double-stranded cDNA was blunt ended with T4 DNA polymerase using a commercial cDNA synthesis kit (obtained from Amersham). After attachment of EcoRI linkers (obtained from Pharmacia), EcoRI digestion, and ligation into EcoRI-digested dephosphorylated M13 tg 130 vector (obtained from Amersham), a cDNA library was obtained by transformation of the *E. coli* TG1 strain. Recombinant plaques ($10^4$) were screened in situ on replica filters with the 1.5 kb. HindIII fragment from clone J19, corresponding to the 3' part of the genome of the $LAV_{BRU}$ isolate of HIV-1, $^{32}$p labelled to a specific activity of $10^9$ cpm/µg. The filters were prehybridized in 5×SSC, 5×Denhardt solution, 25% formamide, and denatured salmon sperm DNA (100 µg/ml) at 37° C. for 4 hours and hybridized for 16 hours in the same buffer (Tm −42° C.) plus 4×$10^7$ cpm of the labelled probe (10⁶ cpm/ml of hybridization buffer). The washing was done in 5×SSC, 0.1% SDS at 25° C. for 2 hours. 20×SSC is 3M NaCl, 0.3M Na citrate. Positive plaques were purified and single-stranded M13 DNA prepared and end-sequenced according to the method of Sanger et al., supra.

Example 4

Hybridization of DNA from HIV-1 and HIV-2 Infected Cells and RNA from HIV-1 and 2 and SIV Virions With a Probe Derived From an HIV-2 Cloned cDNA DNA was extracted from infected CEM cells continuously producing HIV-1 or 2. The DNA digested with 20 μg of PstI, or undigested, was electrophoresed on a 0.8% agarose gel, and Southern-transferred to nylon membrane. Virion dot-blots were prepared in duplicate, as described by F. Clavel et al. in *Science* 233: 343–346 (1986), specifically incorporated herein by reference, by pelleting volumes of supernatant corresponding to the same amount of reverse transcriptase activity. Prehybridization was done in 50% formamide, 5×SSC, 5×Denhardt solution, and 100 mg/ml denatured salmon sperm DNA for 4 hours at 42° C. Hybridization was performed in the same buffer plus 10% Dextran sulphate, and 10⁶ cpm/ml of the labelled E2 insert (specific activity 10⁹ cpm/μg) for 16 hours at 42° C. Washing was in 0.1×SSC, 0.1% SDS for 2×30 min. After exposure for 16 hours with intensifying screens, the Southern blot was dehybridized in 0.4 N NaOH, neutralized, and rehybridized in the same conditions to the HIV-1 probe labelled to 10⁹ cpm/μg.

Example 5

Cloning in Lambda Phage of the Complete Provirus DNA of HIV-2

DNA from the HIV-2ROD infected CEM (FIG. 2, lanes a and c) was partially digested with Sau3AI. The 9–15 kb fraction was selected on a 5–40% sucrose gradient and ligated to BamHI arms of the lambda L47.1 vector. Plaques (2×10⁶) obtained after in vitro packaging and plating on *E. coli* LA 101 strain were screened in situ with the insert from the E2 cDNA clone. Approximately 10 positive clones were plaque purified and propagated on *E. coli* C600 recBC. The λROD 4, 27, and 35 clones were amplified and their DNA characterized by restriction mapping and Southern blotting with the HIV-2 cDNA clone under stringent conditions, and gag-pol probes from HIV-1 used under non stringent conditions.

It will be apparent to those skilled in the art that various modifications and variations can be made in the processes and products of the present invention. Thus, it is intended that the present application cover the modifications and variations of this invention provided they come within the scope of the appended claims and their equivalents.

What is claimed is:

1. A method for the diagnosis of a human immunodeficiency virus type 2 (HIV-2) infection comprising the steps of:
   (a) contacting nucleic acid from a body sample of a person suspected of having an HIV-2 infection with a nucleic acid probe under hybridization conditions of 37° for 16 hours in 5×SSC, 5×Denhardt solution, 25% formamide, and 100 μg/ ml denatured salmon sperm DNA, with washes in 2×SSC, 0.1% SDS at 25°; 1×SSC, 0.1% SDS at 60°; or 0.1×SSC, 0.1% SDS at 60°;
   (b) detecting the formation of the hybrids; and
   (c) correlating the detection of the hybrids with the presence of an HIV-2 infection,
   wherein said nucleic acid probe has the following nucleotide sequence:

```
         10        20        30        40        50
GTGGAAGGCGAGACTGAAAGCAAGAGGAATACCATTTAGTTAAAGGACAG
         60        70        80        90       100
GAACAGCTATACTTGGTCAGGGCAGGAAGTAACTAACAGAAACAGCTGAG
        110       120       130       140       150
ACTGCAGGGACTTTCCAGAAGGGGCTGTAACCAAGGGAGGGACATGGGAG
        160       170       180       190       200
GAGCTGGTGGGAACGCCTCATATTCTCTGTATAATATACCCGCTGCTTG
        210       220       230       240       250
CATTGTACTTCAGTCGCTCTGCGGAGAGGCTGGCAGATTGAGCCCTGGAG
        260       270       280       290       300
GATCTCTCCAGCACTAGACGGATGAGCCTGGGTGCCCTGCTAGACTCTCA
        310       320       330       340       350
CCAGCACTTGGCCGGTGCTGGCAGACGGCCCCACGCTTGCCTGCTTAAAA
        360       370       380
ACCTTCCTTAATAAAGCTGCAGTAGAAGCA.
```

2. An HIV-2 specific nucleic acid probe, wherein said probe is a fragment of HIV-2 nucleic acid deposited at the C.N.C.M. under Accession No. I-627;
   wherein said nucleic acid probe hybridizes to a greater extent to the genomic RNA of HIV-2 than to the genomic RNA of HIV-1 BRU under hybridization conditions of 37° for 16 hours in 5×SSC, 5×Denhardt solution, 25% fornamide, and 100 μg/ ml denatured salmon sperm DNA, with washes in 2×SSC, 0.1% SDS at 25°; 1×SSC, 0.1% SDS at 60°; or 0.1×SSC, 0.1% SDS at 60°.

3. An in vitro diagnostic method for the diagnosis of a human immunodeficiency virus type 2 (HIV-2) infection comprising the steps of:
   (a) contacting nucleic acid from a body sample suspected of containing viral genetic material with a detectable HIV-2 specific nucleic acid probe in a hybridization solution to form a mixture of nucleic acids, wherein said nucleic acid probe is a fragment of HIV-2 nucleic acid deposited at the C.N.C.M. under Accession No. I-627;
   (b) washing the mixture of nucleic acids with a wash solution; and
   (c) detecting the formation of hybrids;
   wherein said hybridization conditions comprise contacting said probe with said nucleic acid from a body sample under hybridization conditions of 37° for 16 hours in 5×SSC, 5×Denhardt solution, 25% formamide, and 100 μg/ ml denatured salmon sperm DNA, with washes in 2×SSC, 0.1% SDS at 25°; 1×SSC, 0.1% SDS at 60°; or 0.1×SSC, 0.1% SDS at 60°; and
   wherein said nucleic acid probe hybridizes to a greater extent to the genomic RNA of HIV-2 than to the genomic RNA of HIV-1 BRU under said hybridization conditions.

4. The method of claim 3, wherein said detection of the formation of a hybridized complex is performed by a process selected from the group consisting of Southern blot, Northern blot, and dot blot.

5. A method for detecting the presence of a human immunodeficiency virus type 2 (HIV-2) comprising:
   (a) providing a sample suspected of containing viral genetic material;
   (b) contacting said sample with an HIV-2 specific nucleic acid probe, wherein said nucleic acid probe is a fragment of HIV-2 nucleic acid deposited at the C.N.C.M. under Accession No. I-627; and (c) detecting the formation of hybrids;

wherein said sample is contacted with said probe in a hybridization solution under hybridization conditions of 37° for 16 hours in 5×SSC, 5×Denhardt solution, 25% formamide, and 100 µg/ml denatured salmon sperm DNA, with washes in 2×SSC, 0.1% SDS at 25°; 1×SSC, 0.1% SDS at 60°; or 0.1×SSC, 0.1% SDS at 60°; and wherein said nucleic acid probe hybridizes to a greater extent to the genomic RNA of HIV-2 than to the genomic RNA of HIV-1 BRU under said hybridization conditions.

6. An isolated HIV-2 nucleic acid, which hybridizes to a probe under hybridization conditions of 37° for 16 hours in 5×SSC, 5×Denhardt solution, 25% formamide, and 100 µg/ml denatured salmon sperm DNA, with washes in 2×SSC, 0.1% SDS at 25°; 1×SSC, 0.1% SDS at 60°; or 0.1×SSC, 0.1% SDS at 60°;

wherein said probe is a fragment of HIV-2 nucleic acid deposited at the C.N.C.M. under Accession No. I-627; and wherein said probe hybridizes to a greater extent to the genomic RNA of HIV-2 than to the genomic RNA of HIV-1 BRU under hybridization conditions of 37° for 16 hours in 5×SSC, 5×Denhardt solution, 25% formamide, and 100 µg/ml denatured salmon sperm DNA, with washes in 2×SSC, 0.1% SDS at 25°; 1×SSC, 0.1% SDS at 60°; or 0.1×SSC, 0.1% SDS at 60°.

\* \* \* \* \*

UNITED STATES PATENT AND TRADEMARK OFFICE
CERTIFICATE OF CORRECTION

PATENT NO. : 6,316,183 B1
DATED : November 13, 2001
INVENTOR(S) : Alizon et al.

It is certified that error appears in the above-identified patent and that said Letters Patent is hereby corrected as shown below:

<u>Column 14,</u>
Line 29, "fornamide" should read -- formamide --.

Signed and Sealed this

Second Day of July, 2002

Attest:

JAMES E. ROGAN
Director of the United States Patent and Trademark Office

Attesting Officer